United States Patent
Smith et al.

(10) Patent No.: US 7,166,825 B1
(45) Date of Patent: Jan. 23, 2007

(54) SOLAR CALIBRATION DEVICE AND METHOD

(75) Inventors: David Stanley Smith, Fort Wayne, IN (US); Kimberly Ann Slack, Fort Wayne, IN (US)

(73) Assignee: ITT Manufacturing Enterprises, Inc., Wilmington, DE (US)

( * ) Notice: Subject to any disclaimer, the term of this patent is extended or adjusted under 35 U.S.C. 154(b) by 0 days.

(21) Appl. No.: 11/130,789

(22) Filed: May 17, 2005

(51) Int. Cl.
G01C 21/02 (2006.01)
G01N 21/47 (2006.01)

(52) U.S. Cl. .................. 250/203.4; 356/446
(58) Field of Classification Search .......... 250/203.4, 250/239, 559.1; 356/447, 448, 139.01
See application file for complete search history.

(56) References Cited

U.S. PATENT DOCUMENTS

| | | | |
|---|---|---|---|
| 4,910,409 A | 3/1990 | Hoffman | |
| 5,302,823 A | 4/1994 | Franklin et al. | |
| 5,384,661 A * | 1/1995 | Geyer et al. | 359/894 |
| 5,594,236 A * | 1/1997 | Suzuki et al. | 250/214.1 |
| 5,659,168 A | 8/1997 | Dey et al. | |
| 5,716,030 A | 2/1998 | LaFiandra et al. | |
| 5,835,267 A | 11/1998 | Mason et al. | |
| 6,005,249 A | 12/1999 | Hayes, Jr. et al. | |
| 6,017,001 A * | 1/2000 | Lambeaux et al. | 244/169 |
| 6,111,640 A | 8/2000 | Hedman et al. | |
| 6,455,830 B1 | 9/2002 | Whalen et al. | |
| 6,597,457 B1 * | 7/2003 | Silverglate et al. | 356/446 |
| 2003/0230725 A1 * | 12/2003 | Wong | 250/372 |

FOREIGN PATENT DOCUMENTS

FR  2 730 808 A1  2/1995

* cited by examiner

*Primary Examiner*—Georgia Epps
*Assistant Examiner*—Pascal M. Bui-Pho
(74) *Attorney, Agent, or Firm*—RatnerPrestia

(57) ABSTRACT

A solar calibration device for a remote sensor having a housing having a deployable door at one portion of the housing and an aperture at another portion of the housing is provided. Disposed in the housing is a solar diffuser for receiving solar irradiance when the deployable door is in an open position, and diffusely reflecting the received solar irradiance. A solar diffuser monitor also disposed within the housing receives diffusely reflected solar irradiance from the solar diffuser, for calibrating the solar irradiance reflected from the solar diffuser, and receives solar irradiance directly from the sun through the aperture to calibrate the spectral reflectance of the solar diffuser monitor detectors based on the solar irradiance received directly from the sun.

19 Claims, 8 Drawing Sheets

SOLAR CALIBRATION DEVICE AND METHOD

The present invention is directed to energy calibration equipment used in spacecraft, and more particularly, to calibration equipment for remote sensing devices.

BACKGROUND OF THE INVENTION

Spacecraft such as probes and satellites generally support devices having energy detecting capabilities of one type or another. Remote sensing devices such as infrared, optical, and radio telescopes are examples of such detecting devices. Typical remote sensing devices provide measurement of reflected (primarily solar) or emitted (from man-made sources) visible and near-infrared energy from the Earth or other heavenly bodies. A method of calibrating the measured radiance from Earth (or other source) is to create a reference radiance using a ubiquitous, known source of spectral irradiance, such as the Sun, as reference input to a diffusive reflector which in turn provides a known radiance to the remote sensing instrument aperture.

The standard radiance value may be created by reflecting known solar spectral irradiance from the diffuser panel toward the remote sensing device during an occasional (non-normal operation) calibration. The remote sensing device output is measured as the device receives the known diffusely reflected energy from the diffuser panel. Using the linear characteristics of the remote sensing device and a reference view of empty space (i.e., no significant irradiance at the remote sensing device aperture), response of the device to the known radiance input is determined. This radiance calibration process provides sufficient information to calculate radiance incident at the device aperture during normal operation using the instrument output as it views the Earth or other target of interest.

The spectral reflectance characteristics of the diffuser panel, however, may change with time due to degradation of the diffuser panel. Since the diffuser panel is employed as the reference source, any change, i.e., degradation of the diffusive surface material, results in a distortion in the measurements of the remote sensing device.

According to U.S. Pat. No. 5,716,030, an attempt is made to prevent the diffuser surface from degrading by providing a door having a first calibration surface disposed on a first panel to provide a radiant temperature reference for infrared calibrations. A second calibration surface is disposed on a second panel to provide an absolute radiance reference for optical calibrations. A hinge controls the relative positioning of the calibration and reference panels with respect to each other and with respect to the remote sensor.

Another method of accounting for diffuser surface degradation, according to U.S. Pat. No. 6,597,457, is through a device that calibrates the diffuser panel by sighting the sun via a port, and detecting the intensity of radiation within an averaging chamber in which a remote sensor is disposed. The radiation averaging chamber is constructed in a spherical shape having a diffuse inner reflecting surface to induce multiple reflection of radiation to accomplish an averaging of the radiation. Two ports are provided in a wall of the chamber for entry of radiation, a first port is employed for viewing solar radiation reflected by the diffuser panel, and a second port is employed for sighting solar radiation propagating directly from the sun to the second port.

SUMMARY OF THE INVENTION

A solar calibration device for a remote sensor having a housing having a deployable door at one portion of the housing and an aperture at another portion of the housing is provided. Disposed in the housing is a solar diffuser for receiving solar irradiance when the deployable door is in an open position, and diffusely reflecting the received solar irradiance. A solar diffuser monitor having detectors is also disposed within the housing. The solar diffuser monitor receives diffusely reflected solar irradiance from the solar diffuser for calibrating the solar irradiance reflected from the solar diffuser. The solar diffuser monitor also receives solar irradiance directly from the sun thorough the aperture to calibrate the solar diffuser monitor detectors.

The present invention is also directed to a solar calibration method. The method includes transmitting solar irradiance into a housing using a deployable door disposed at one portion of the housing and an aperture disposed at another portion of the housing; reflecting the transmitted solar irradiance, using a solar diffuser disposed within the housing, when the deployable door is in an open position; receiving, by a solar diffuser monitor having detectors, reflected solar irradiance from the solar diffuser for calibration of the solar diffuser, and receiving, by the solar diffuser monitor, solar irradiance directly received from the aperture for calibrating the solar diffuser monitor detectors.

A method of calibrating a diffusive surface of a solar calibration device according to another exemplary embodiment of the present invention includes positioning a remote sensor to receive reflected solar radiation from a diffusive surface for calibration of the remote sensor; positioning a monitor to receive direct solar radiation for calibration of the monitor; positioning the monitor to receive a non-illuminated spectral measurement of the diffusive surface; deploying a door to an open position to expose the diffusive surface to solar irradiance; simultaneously measuring spectral values, using the remote sensor and the monitor, of radiation reflected from the diffusive surface; deploying the door to a closed position; positioning the remote sensor to image the earth; and positioning the monitor to a stowed position.

BRIEF DESCRIPTION OF THE DRAWINGS

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures.

DETAILED DESCRIPTION OF THE INVENTION

The present invention is directed to monitoring the rate of degradation of a reflective solar diffusive surface used as a reference source for a remote sensor on board a spacecraft, as the spacecraft orbits the earth. The diffusive surface is monitored with a diffuser monitor. The diffuser monitor measures the amount of solar radiance from the diffusive surface, when the diffusive surface first enters service. Thereafter, the diffuser monitor periodically measures the amount (relative amount) of spectral solar radiance reflected from the diffusive surface and develops a history of these measurements. Degradation may be observed over time, as the diffuser monitor reports a change in intensity of solar spectral radiance reflected from the diffusive surface.

Additionally, the diffuser monitor performs a self-check on its own performance, by periodically measuring direct solar irradiance from the sun, that is, the diffuser monitor checks its own spectral measuring stability. By trending measurements of well-characterized, direct solar irradiance from the sun, the diffuser monitor verifies its ability to accurately measure solar radiance, either reflected from the diffusive surface or direct solar irradiance. The data collected by the diffuser monitor, i.e., the reflected radiance from the diffusive surface and the direct solar irradiance, may be transmitted back to the earth for analysis or may be transmitted directly to the remote sensor for recalibration of the remote sensor.

A diffusive surface used as a reference source for a remote sensor according to an exemplary embodiment of the present invention includes a solar diffusive surface. One such source material is a white reflecting material. One particular white reflecting material is a thermoplastic resin material sold under the trade name Spectralon™ manufactured by Labsphere of North Sutton, N.H. Spectralon™ has a hardness roughly equal to that of high-density polyethylene and is thermally stable to greater than 350° C. It is chemically inert to all but the most powerful bases such as sodium amide and organo-sodium or lithium compounds. It is also extremely hydrophobic. Spectralon™ reflectance material has a high diffuse reflectance compared to known materials or coatings over the Ultraviolet-Visible-Near infrared (UV-VIS-NIR) region of the spectrum. Spectralon™ spectral reflectance is high and spectrally flat in the very near infrared (VNIR) region and slightly lower, but just as consistent in the short wave infrared (SWIR) region. The reflectance is generally greater than 99% over a range from 400 to 1500 nm and greater than 95% from 250 to 2500 nm. Space-grade Spectralon™ combines high-reflectance with an extremely Lambertian reflectance profile and is the material of choice for terrestrial remote sensing applications.

Figure 1:
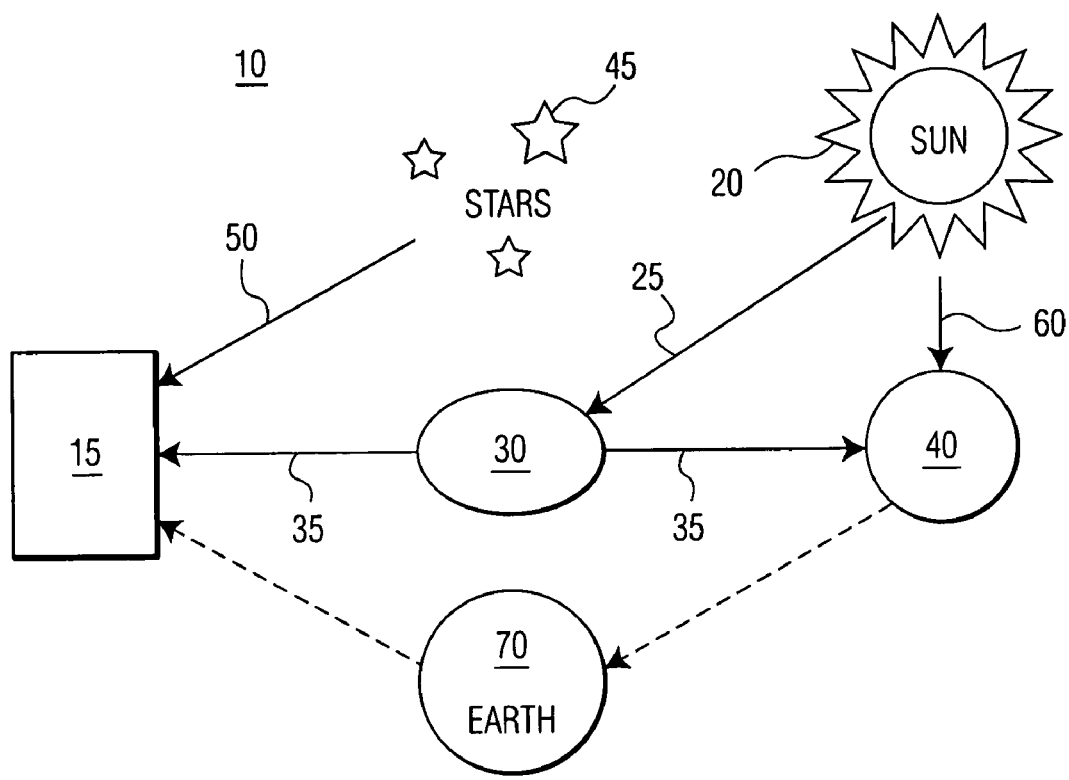
FIG. 1 is a schematic representation of a solar calibration process for a remote sensor.

Referring now to the drawings, in which like reference numbers refer to like elements throughout the various figures, FIG. 1 is a schematic representation of a solar calibration process 10 for a remote sensor. As used throughout, an exemplary remote sensor may be an Advanced Baseline Imager (ABI). Remote sensor 15 may measure radiance reflected from the earth 70. To calibrate remote sensor 15, various input signals may be used. For example, stellar irradiance 50, received from stars 45, may be used, as shown in FIG. 1. In addition, sun 20 may provide spectral irradiance 25 to reflective diffusive surface 30, which in turn provides reflected radiance 35 to remote sensor 15. As will be explained in detail, solar diffuser monitor (SDM) 40 may also be used to calibrate the diffusive surface by receiving reflected radiance 35 from diffusive surface 30. As will also be explained, SDM 40 may separately receive direct solar irradiance 60 from sun 20, to be used as a self-check on its own spectral measuring stability. In addition, SDM 40 has a stowed position, where it is substantially shielded from ionizing radiation from the orbital environment.

Figure 2:
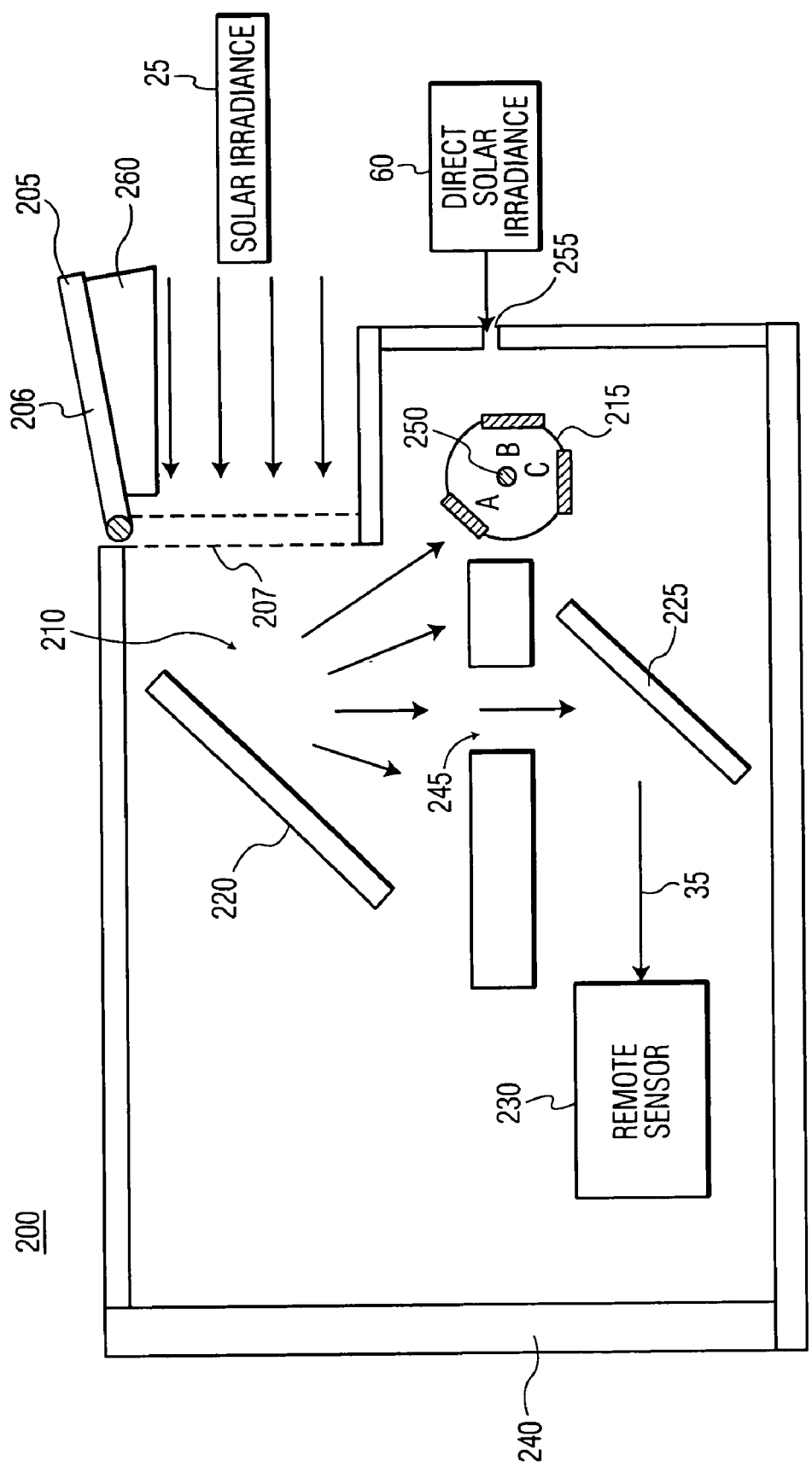
FIG. 2 is schematic view of a solar calibration device according to an exemplary embodiment of the present invention.

Referring now to FIG. 2, there is shown a schematic diagram of solar calibration device 200, according to an exemplary embodiment of the present invention. Solar calibration device 200 includes a substantially sealed housing 240 having door 205 with contamination guard 260. Housing 240 contains SDM 215 (shown in positions A, B and C) positioned by motor 250, diffusive plate 220, scanner 225, and remote sensor 230. According to an embodiment scanner 225 is a scanning mirror. The housing permits sunlight to enter by way of deployable door 205 and by way of small apertures 255.

Figure 3:
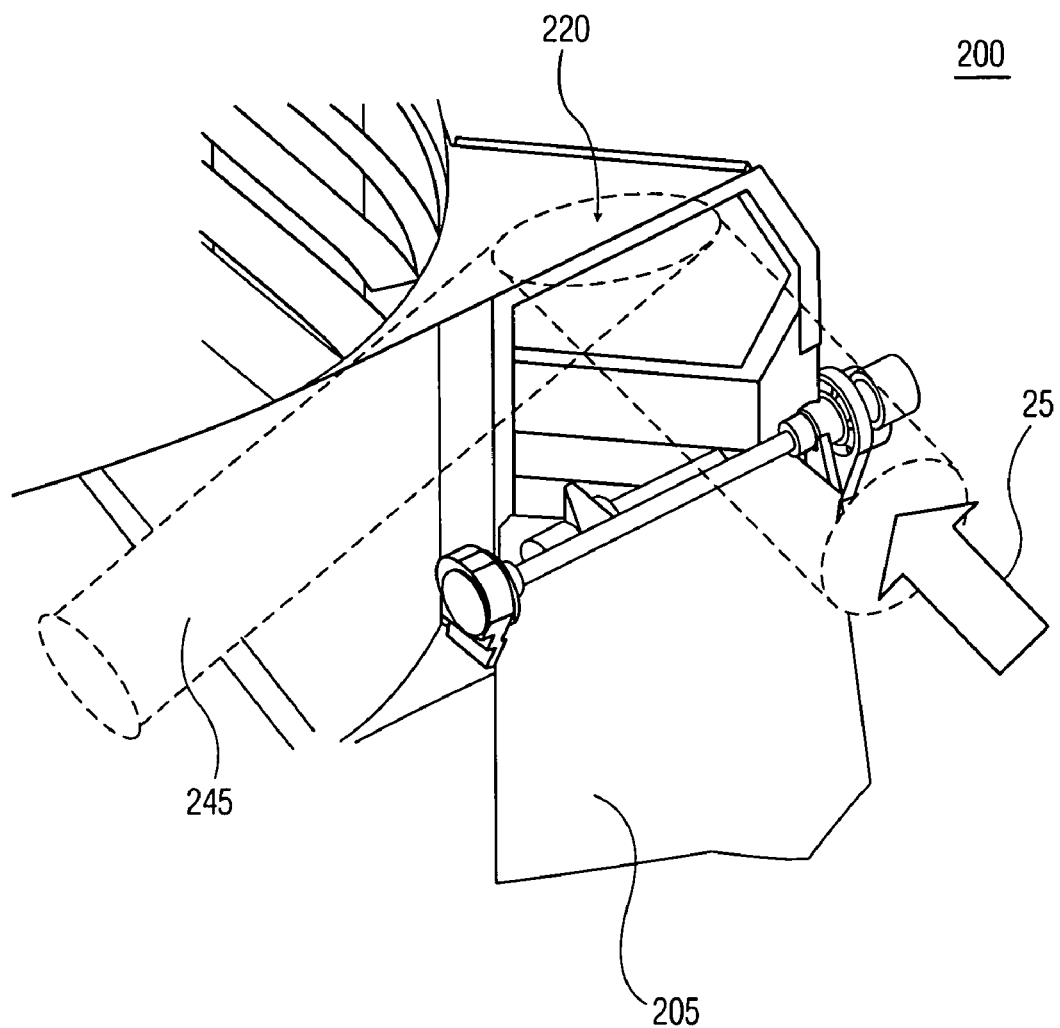
FIG. 3 is a schematic illustration of solar irradiance entering a solar calibration device according to an exemplary embodiment of the present invention.

Attached door 205 is deployable to an open position (shown as open door 206) and to a closed position (shown by dashed lines as closed door 207). Referring now to FIG. 3, when deployable door 205 is in the open position solar irradiance 25 enters solar calibration device 200 and strikes diffusive plate 220. Diffuse radiance is reflected off diffusive plate 220 and into aperture 245. According to an exemplary embodiment, aperture 245 may have a diameter of 13 cm. After the solar radiance passes through aperture 245, it impinges upon scanner 225 (shown in FIG. 2). Scanner 225 sends the radiation to remote sensor 230 (also shown in FIG. 2).

Although not shown in FIG. 2 but can be appreciated, when door 205 is in closed position 207, contamination guard 260 seals calibration device cavity 210 including aperture 245. A stepper motor (not shown) controls the movement of door 205. When door 205 is in open position 206, solar irradiance strikes diffusive plate 220, which reflects radiance toward both scanner 225 and SDM 215. SDM 215 receives reflected solar irradiance from diffusive plate 220, when SDM 215 is in position A, as will be discussed in detail below. Additionally, diffusive plate 220 reflects solar radiance toward scanner 225 which, in turn, transmits diffused radiance 35 to remote sensor 230.

Solar irradiance may also enter housing 240 by way of precision pinhole apertures 255 (only one aperture is shown in FIG. 2). Each pinhole aperture is aligned with a respective detector of SDM 215 (detectors 705, 710 of SDM 215 are shown in detail in FIG. 7). Direct solar irradiance 60, entering through aperture 255, strikes SDM 215, when the SDM is oriented in position B. SDM 215 may be oriented in three different positions by way of stepper motor 250. The three different orientations are shown schematically as positions A, B, and C. (The SDM may only be in one position at any one time.)

Figure 4:
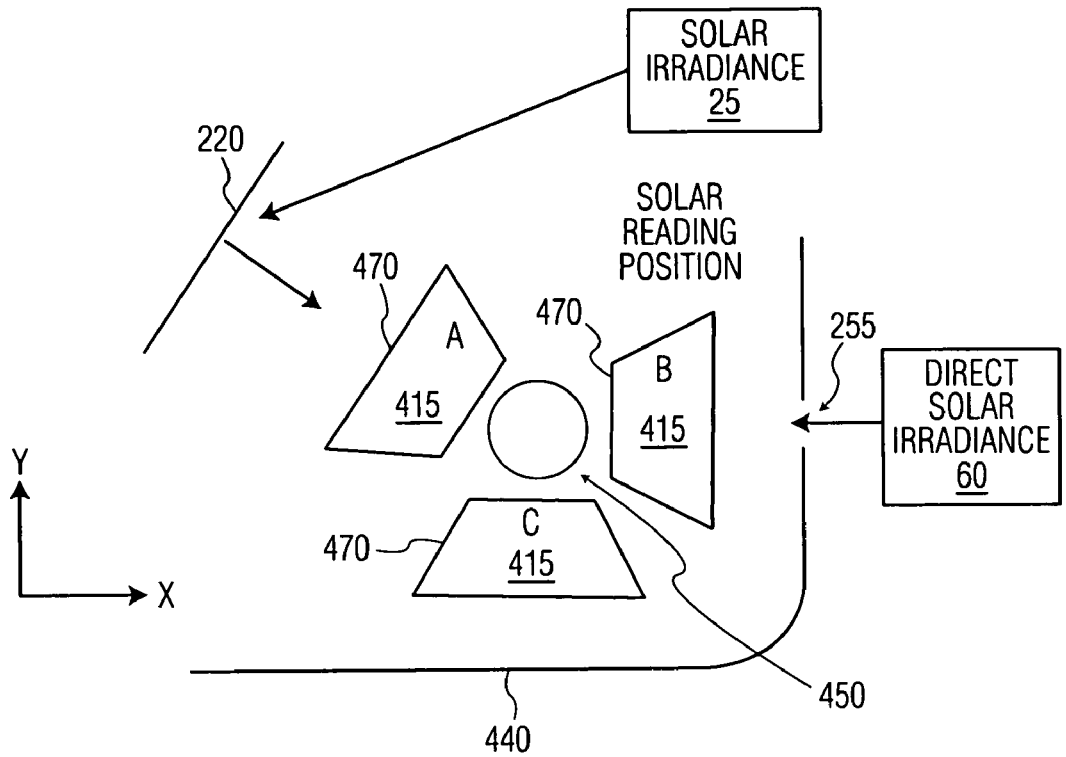
FIG. 4 is a schematic illustration of the positions of the solar diffuser monitor according to an exemplary embodiment of the present invention.

FIG. 4 is a schematic illustration of three different positions of SDM 415 that corresponds to three positions A, B, and C of SDM 215 shown in FIG. 2. As shown, SDM 415 includes detector surface 470. Motor 450 rotates SDM 415 to orient detector surface 470 to the three different positions. For example, in position A, SDM detector surface 470 is oriented to receive reflected solar radiance from diffusive plate 220. In position B, SDM detector surface 470 is oriented to receive direct solar irradiance through apertures 255 (only one shown).

It will be appreciated that solar irradiation and space contamination degrade instruments and electronics of space-borne equipment. Therefore, by limiting the time the SDM is in positions A and B, the usefulness of the detectors of SDM 415 may be extended. Consequently, SDM 415 may be placed in a stowed mode, or a sleep mode, when the SDM is oriented in position C. Shield 440 provides further protection from contamination, for example, protection from radiation (shown in more detail in FIG. 7). Shield 440 may be constructed from aluminum with a thickness ranging between 0.1 inch to 0.3 inch, or greater.

The diffusive surface of plate 220 is first measured in a laboratory before installation in housing 240, in order to obtain the baseline reflective qualities of the surface. The baseline reflective qualities of the diffusive surface are characterized by measuring its bi-directional reflectance factor (BRF). According to one method for measuring the reflective characteristics of the diffusive surface as a function of incidence angle, the BRF characteristics are determined in a laboratory by comparing them against a pressed polytetrafluoroethylene (PTFE). For example, one PFTE, sold under the trade name Algoflon®, is manufactured by Solvay Solexis of Thorofare, N.J. and is made in accordance with standards set by the National Institute of Standards and Technology. Algoflon® has a known directional hemispherical reflectance and 45°:0° reflectance ratio. The reflectance measurements for Algoflon® and the reflective solar diffuser plate are taken simultaneously and the resulting values are expressed as a ratio set forth in equation 1 below.

Equation 1: Bidirectional Reflectance Factor ratio of sample to Algoflon®

$$BRF_{sample}(\theta_i, \phi_i, \theta_r, \phi_r, \lambda) = \frac{\Phi_{sample}(\theta_i, \phi_i, \theta_r, \phi_r, \lambda)}{\Phi_{lambertain}(\theta_i, \phi_i, \theta_r, \phi_r, \lambda)}$$

where:
- $\theta_i$ = incident zenith angle
- $\phi_i$ = incident azimuth angle
- $\theta_r$ = reflected zenith angle
- $\phi_r$ = reflected azimuth angle
- $\lambda$ = wavelength (microns)
- $\Phi_{sample}$ = reflected flux from sample (W/μm)
- $\Phi_{lambertian}$ = reflected flux from Lambertian reflector (W/μm)

The BRF of Algoflon® is calculated by equation 2:

Equation 2: Bidirectional Reflectance Factor of Algoflon as measured by NIST $$BRF_{Algoflon®}(\theta_i, \theta_r) = BRF_{Algoflon®}(45°, 0) \times B(\theta_i, \theta_r)$$

Where the ratio shown in equation 3 may be used:

Equation 3: Ratio of radiometer signal ($S_{Algoflon}$) to determine directional reflectance $$B(\theta_i, \theta_r) = \frac{S_{Algoflon®}(\theta_i, \theta_r)/\cos(\theta_i)}{S_{Algoflon®}(45°, 0)/\cos(45°)}$$

where $S_{Algoflon®}$ is the signal (voltage) from the radiometer with dark current subtracted. Finally, the BRF of the sample is determined using equation 4:

Equation 4: Ratio method to determine BRF of sample $$BRF_{sample}(\theta_i, \theta_r) = \frac{S_{sample}(\theta_i, \theta_r)}{S_{Algoflon®}(\theta_i, \theta_r)} \times BRF_{Algoflon®}(\theta_i \theta_r)$$

Once the reflectance characteristics of the diffusive surface are characterized and known, the diffusive surface may be mounted in an instrument and its baseline reflectance characteristics may be used as a spectral standard for a remote sensor in a spacecraft.

Figure 5:
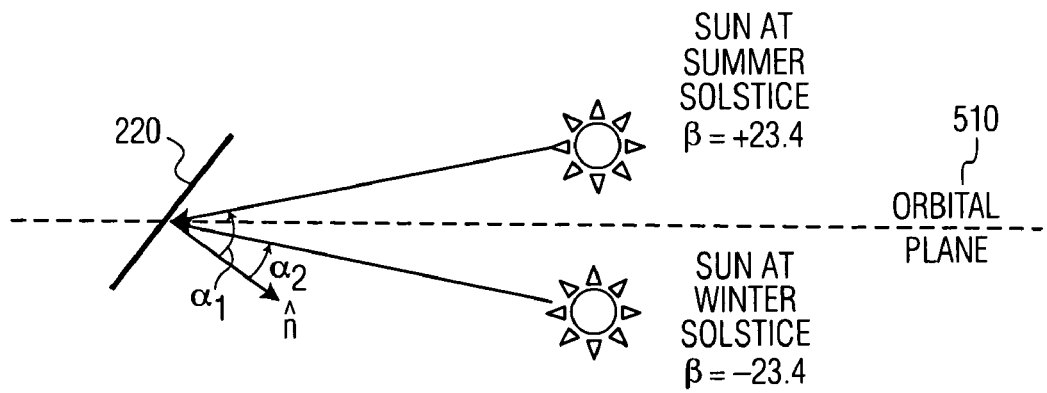
FIG. 5 illustrates the range of incidence angles of solar irradiance with respect to a diffusive surface according to an embodiment of the present invention.

In addition to knowing the reflectance characteristics of the diffusive surface, the incident angle of the solar irradiance must also be known as a function of time of year. FIG. 5 illustrates variations in the incident angle of solar irradiance striking the diffusive surface, as the solar calibration device travels along orbital plane 510. Diffusive plate 220, according to an embodiment of the invention, is fixed into solar calibration housing 240 at an orientation of 45° in yaw (about the Z axis) and 19° in pitch (around the Y axis).

The sun moves through the spacecraft's orbital plane 510. For example, as shown in FIG. 5, during the summer and winter solstices, the sun is +/−23.4°, respectively, from the orbital plane. The solar radiance, as reflected off the diffuser, is weighted with a cosine function. The angular argument for the cosine function is with respect to the normal vector of the diffuser. $\alpha_2$ is the minimum angle (~21.6°)(winter solstice)

and therefore will have the largest calibration albedo (radiance) value. $\alpha_1$ is the maximum angle (~68.4°) and therefore will have the smallest calibration albedo (radiance) value. Direction cosines are used to establish projected areas of reflected solar radiance. Two direction cosine terms are used, corresponding to the angle between the SDM normal and the sun (($\phi_{sunsd}$) and the angle between the SDM and the north/south scan mirror ($\theta_{sd\_sm}$).

The angle between the SDM and scan mirror is fixed, so the direction cosine term is constant. The sun, however, changes its position with respect to the instrument by approximately 50°. The large differences in angle of incidence (AOI) affects the amount of flux entering the system, so a cosine term is used to characterize that variation. These cosine terms are calculated for the angular range of the sun's movement and stored in a lookup table (LUT). During a calibration sequence, the position of the sun with respect to the SDM normal vector is determined and that direction cosine is used in the effective input radiance calculation, discussed below.

Figure 6:
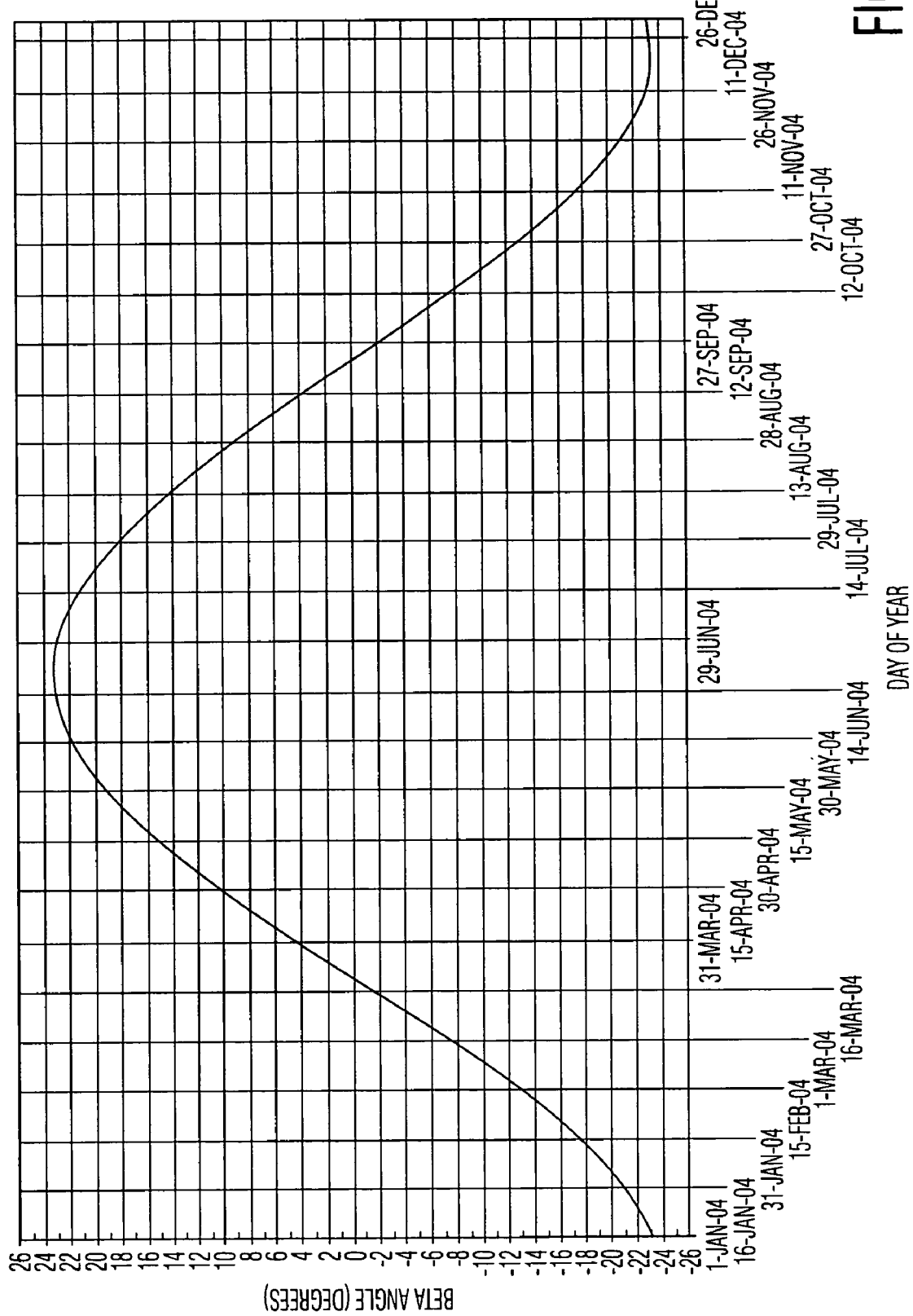
FIG. 6 is a plot of the solar incident irradiance angles with respect to time.

FIG. 6 is a plot of the angle of the sun's position with respect to the Earth's equatorial plane (referred to as Beta Angle) as a function of time over a one-year period. Beta angles also affect the ability of the SDM to perform its self-calibration spectral measuring stability check, discussed in more detail with respect to FIG. 8.

Figure 7:
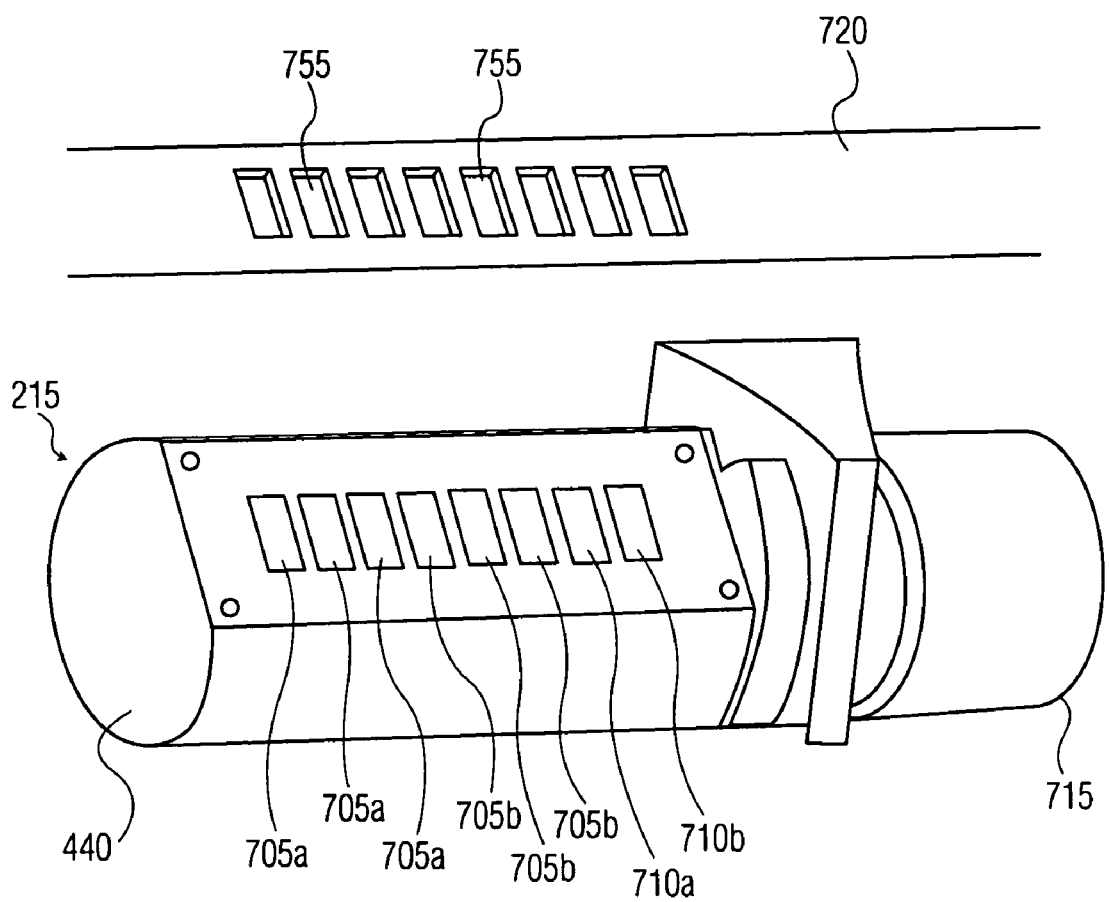
FIG. 7 shows an exemplary embodiment of a solar diffuser monitor of the present invention.

According to an exemplary embodiment of the present invention, the SDM measures both the reflectance from the diffusive plate and the direct solar irradiation by using four detectors, (4 are active, 4 are redundant in case of primary electronics box failure) as shown in FIG. 7. These detectors have identical optical spectral bandpass (or envelope) as the array of detectors of the remote sensor. The visible and near infrared (VNIR) spectral bands are bridged using two different detector technologies, based on InGaAs and silicon.

SDM 215 includes a dual set (705a and 705b) of three (3) silicon photodiodes, each tuned by a bandpass filter (not shown) to a different spectral envelope with center wavelengths of 0.47, 0.64, and 0.86 microns. Also included in the SDM is a dual set (710a and 710b) of one (1) InGaAs photodiode, each tuned by a bandpass filter to the center wavelength 1.38 microns. The dual sets of silicon detectors and InGaAs detectors provide redundancy to the SDM. Housing 440 of SDM detector 215 shields the detector from potentially damaging ionizing particles associated with the geostationary orbit environment.

Although not shown, it will be appreciated that the SDM includes a CMOS transimpedance amplifier that offers adequate gain and low input offset current for each detector. To increase stability, a feedback resistor in the amplifier may be of a highly radiation-resistant thin-film type. The bandpass optical filters of SDM 215 are tuned to the same spectral bandpass used by the remote sensor. The filters of the SDM and the filters of the remote sensor may be manufactured from the same substrates/coating lots, in order to reduce spectral uncertainty. In addition, InGaAs detectors 710a and 710b are more radiation resistant than silicon detectors 705a and 705b. The rate of change of the SDM detector response from band to band may be used as one indication of the stability of the SDM detectors in trending algorithms.

As also shown in FIG. 7, SDM 215 is coupled to motor 715 to orient the SDM (as described previously) to (1) observe radiant energy from a diffusive surface or (2) observe irradiant energy directly from the sun. The motor also orients the SDM into a third position, namely the stowed position. Motor 715 may be a four-phase stepper motor or any other suitable motor known by one skilled in the art.

For discussion purpose, SDM 215 is shown positioned adjacent and opposite to aperture plate 720. Formed in aperture plate 720 is a series of precision pinhole apertures, designated as 755. It will be appreciated that pinhole apertures 755 correspond to apertures 255 (one shown) of FIGS. 2 and 4. When SDM 215 is in position B for receiving direct solar irradiance (FIGS. 2 and 4), apertures 755 are coincident with detectors 705a, 705b, 710a, and 710b.

To account for the possibility that the detectors of the solar diffuser monitor may themselves be degrading over time, the present invention uses the SDM to perform a self-check on its own detectors, by periodically measuring direct solar irradiance from the sun. In this manner, the diffuser monitor may check its spectral measuring stability. SDM measurement of direct solar irradiance is trended over time and any change in spectral measurement is an indication that the SDM detectors may be degrading. These direct solar irradiance measurements are taken twice a year, near equinoxes.

The invention further contemplates that the trending data of the SDM may be transmitted to earth for analysis and recalibration of the remote sensor by data uplink, as shown schematically in FIG. 1 by SDM 40 transmitting data to earth 70 and earth 70 uplinking results of the analyzed data to remote sensor 15. As an alternative, the trending data from SDM 40 may be directly transmitted to remote sensor 15 by SDM 40 for recalibrating the remote sensor's measured spectral standard values.

The inventors have determined that if less than 50% radiance level is used, the direct solar calibration cycle may be increased to four months per period, providing a total of 8 months worth of data per year.

Figure 8:
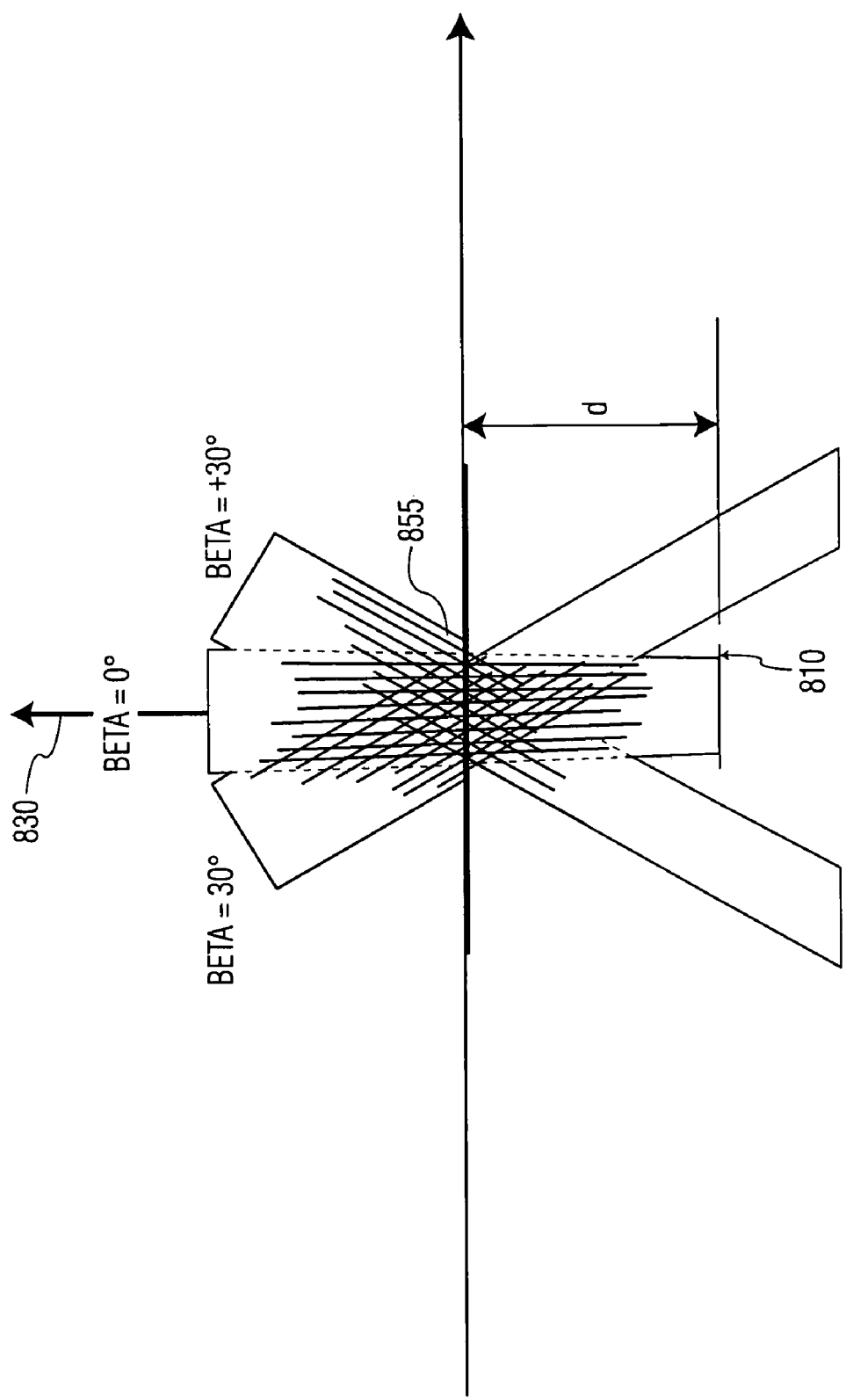
FIG. 8 illustrates the relationship of precision pinhole apertures and the detectors of the solar diffuser monitor to the seasonal positioning of the sun according to an exemplary embodiment of the present invention.

Referring next to FIG. 8, there is shown a relationship between the SDM's detectors and their corresponding apertures and their geometry with respect to the sun. The apertures are shown in FIG. 8 as rectangles, however, according to another embodiment, the apertures may also be circular. For clarity, FIG. 8 shows only one aperture 855 and one detector 810, which correspond, respectively, to a single aperture 755 and a corresponding single detector 705, 710, shown in FIG. 7. FIG. 8 illustrates three ray traces having a β angle of −30°, 0, and +30°, respectively, with respect to perpendicular axis 830 (or aperture normal vector) extending from the center of aperture 855 and detector 810.

Precision pinhole aperture 855 and detector 810 are sized such that incident solar irradiance, having a β angle of approximately 0°, would fully impinge upon detector 810. According to an exemplary embodiment, aperture 855 has a radius of 395 μm, detector 810 has a radius of 500 μm, and the distance d between aperture 855 and detector 810 is approximately 2000 μm. Rays of −30° and +30° are extreme maximum and minimum angles and, as shown, do not impinge upon detector 810. The SDM calibrated itself off of solar irradiance through these pinhole apertures. However, because the plate is fixed, the SDM is only able to observe sunlight at certain times of year. This figure demonstrates that maximum flux is obtained through the aperture at Beta=0, during the two equinox seasons. Because of the size and distance relationships between aperture 855 and detector 810, only solar rays having a β between approximately −10° and +10° partially or fully impinge upon detector 810.

Table 1 shows an exemplary solar calibration cycle for solar calibration device 200. The first column shows the steps in the calibration cycle. The second column describes the movement of the various elements (scanner 225, SDM 215, door 205) during each step. The third column identifies the data collected during a corresponding calibration step. The last column provides an exemplary duration of each step.

TABLE 1

Solar Calibration Device Operation Cycle
Solar Calibration Cycle

| Step | Description | Data | Time (sec) |
|---|---|---|---|
| 1 | Scanner positioned for space look | Remote Sensing Instrument Zero radiance (offset) 1st gain point | 2.5 |
|  | SDM views sun (around equinox) | SDM absolute reference, gain, SDM position indication |  |
| 2 | Scanner moves to view Reflective Diffuser Plate | 2nd Point of 2-point gain determination | 2 |
|  | SDM views non-illuminated Reflective Diffuser Plate | SDM Zero radiance (offset) |  |
| 3 | Calibration Door Opened (Sun irradiates Reflective Diffuser Plate) | Door open signal | 10 |
| 4 | Solar Calibration Data Gathered | Albedo measurement 256 samples | 2.5 |
|  | SDM measurement of Reflective Diffuser Plate | Reflective Diffuser Plate meas. |  |
| 5 | Door Closes | Door closed signal | 10 |
|  | Scanner returns to operation | Mode scan telemetry |  |
|  | SDM returns to sleep position | SDM dark reference, SDM position signal |  |
|  | Total |  | ~30 |

Figure 9:
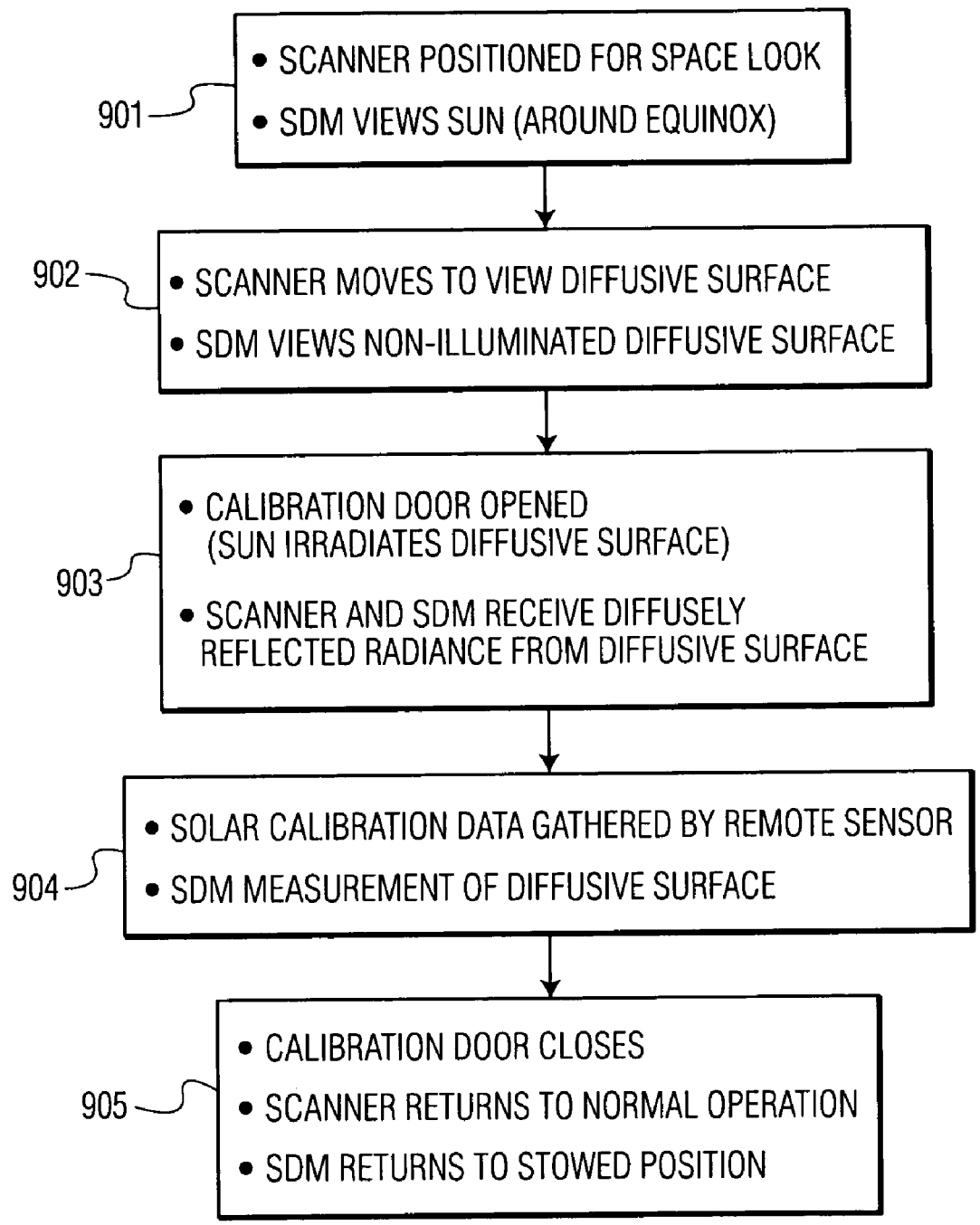
FIG. 9 illustrates an exemplary calibration method according to an embodiment of the present invention.

The calibration method is further described with respect to FIG. 9. The method begins with step 901 moving scanner 225 into position for a space look. While door 205 stays closed, the method obtains a zero radiance offset first gain point for remote sensor 230. During the same time, the SDM is positioned to directly view the sun through precision aperture plate 255 (this portion of step 901 is performed proximal to the time of equinox, +/−1 month). The sun's spectral irradiance is measured at the aperture plate as seen in FIG. 8. This portion of the step is used to obtain trending data (over several months) to establish the relative SDM spectral stability. If the trending data does not change, the present invention confirms that the SDM is stable and corrections for SDM degradation are not necessary. Furthermore, the time during which the SDM is exposed to the sun during equinox is minimal and, therefore, minimal degradation of the SDM detectors are expected.

After baseline parameters are established, the method enters step 902 to position the scanner and SDM to receive incident solar radiance from reflective solar diffuser plate 220. During this step, the deployable door is still closed. The SDM moves into position A and acquires a dark image of the diffusive surface. The SDM now establishes a zero radiance offset.

Next, step 903 opens the deployable door. Solar irradiance strikes the diffusive surface, which reflects radiance simultaneously onto the SDM and the scanner. The method then enters step 904, in which (a) the SDM measures the diffusely reflected solar radiance and (b) the remote sensor obtains data to use for its calibration. The deployable door closes in step 905. The scanner returns to its normal operating position and the SDM returns to its stowed position, where the latter is substantially shielded from contamination and radiation.

The SDM measures the diffusive surface each time the remote sensor receives solar irradiance for its calibration. By trending the measured spectral values over time, the SDM is able to determine that the diffusive surface is degrading and, therefore, the SDM data can be used to correct the calibration that was independently obtained by the remote sensor. On initial calibration, the BRF of the diffusive surface calculated in the laboratory discussed above is used. Trending of diffuser degradation can be performed (to projected overall degradation at the shorter wavelengths) by ratioing over the initial measurement taken on orbit.

The following equation calculates effective radiance of the diffuser:

$$\langle L(\lambda) \rangle_{diffuser} = \frac{\int_0^\infty \eta(\phi, \theta, \lambda) * E_{sun}(\lambda) * \Phi(\lambda) * BRF(\theta_i, \theta_r, \lambda) * \cos(\theta_\oplus) d\lambda}{\int_0^\infty \Phi(\lambda) d\lambda} = m * dn$$

$\eta(\phi, \theta, \lambda)$ is a polarization term;
$E_{sun}(\lambda)$ is solar irradiance;
$\Phi(\lambda)$ is the spectral response of the particular channel;
BRF is the Bi-directional reflectance factor of the diffuser;
$\cos(\theta_\oplus)$ angle between the diffusive surface normal vector and the sun;
m is inverse responsivity of the spectral channel; and
dn is the digital counts where $dn=DN_{diffuser}-DN_{space}$.

Trending the diffuser degradation is calculated by:

$$BRF_{cal}(\theta_i, \lambda) = \frac{dn(\theta_i, \lambda)_{new}}{dn(\theta_i, \lambda)_{previous}} * BRF(\theta_i, \lambda)_{previous}$$

$BRF_{cal}$ is the Bi-Directional Reflectance Factor applied to the effective diffuser radiance equation;
$dn(\theta_i, \lambda)$new is the most recent digital counts produced from the most recent calibration;
$dn(\theta_i, \lambda)_{previous}$ is the digital counts produced from the last calibration; and
$BRF_{previous}$ is the BRF calculated from the previous calibration.

Although the invention is illustrated and described herein with reference to specific embodiments, the invention is not intended to be limited to the details shown. Rather, various modifications may be made in the details within the scope and range of equivalents of the claims and without departing from the invention.

What is claimed is:

1. A solar calibration device for a remote sensor comprising:
 a housing having a deployable door at one portion of the housing and an aperture at another portion of the housing;
 a solar diffuser disposed within the housing for receiving solar irradiance, when the deployable door is in an open position, and diffusely reflecting the received solar irradiance;
 a solar diffuser monitor having detectors, disposed within the housing, receiving the diffusely reflected solar irradiance from the solar diffuser, for calibrating the solar irradiance reflected from the solar diffuser, and
 the solar diffuser monitor receiving solar irradiance directly from the sun through the aperture, and calibrating the solar diffuser monitor detectors based on the solar irradiance received directly from the sun,
 wherein the solar diffuser monitor is pivoted between first and second positions, and
 the first position is configured to receive the diffusely reflected solar irradiance from the solar diffuser, and the second position is configured to receive the solar irradiance directly from the sun through the aperture.

2. The device of claim 1 wherein
 the solar diffuser monitor is pivoted between first, second and third positions, and
 the third position is configured to substantially prevent the solar diffuser monitor from receiving solar irradiance directly from the sun and solar radiance reflected from the solar diffuser.

3. The device of claim 2 wherein
 the solar diffuser monitor further comprises an aluminum shield disposed about the solar diffuser monitor.

4. The device of claim 1 wherein
 the solar diffuser monitor includes a plurality of photodiode detectors.

5. The device of claim 4 wherein
 one of the photodiode detectors is positioned directly opposite the aperture having a predetermined diameter size,
 the one photodiode detector is spaced at a predetermined distance from the aperture, and
 the predetermined diameter size and the distance are configured to permit direct solar irradiance to impinge on the photodiode detector, at an angle of substantially 0° with respect to a normal line passing through the aperture and the photodiode detector.

6. The device of claim 4 wherein
 the photodiode detectors include a first set of three silicon diodes and a second set of InGaAs diodes.

7. The device of claim 6 wherein
 each diode of the first set of three silicon diodes is tuned to a different wavelength, and
 each diode of the second set of InGaAs diodes is tuned to a wavelength different from the wavelengths of the first set of three silicon diodes.

8. The device of claim 6 wherein
 the first set of three silicon diodes are tuned by respective filters to a center wavelength of 0.47, 0.64, and 0.86 microns, and
 the second set of InGaAs diodes are tuned by respective filters to a center wavelength of 1.38 microns.

9. The device of claim 8 wherein
 the remote sensor includes an advanced baseline imager (ABI) having an array of detectors.

10. The device of claim 9 wherein
 the array of detectors of the remote sensor are tuned to substantially the same wavelengths as the respective wavelengths of the first and second sets of diodes.

11. The device of claim 1 wherein
 the remote sensor receives radiation reflected from the solar diffuser by way of a scanner disposed downstream from the solar diffuser, and
 a scanner aperture is disposed between the scanner and the solar diffuser.

12. The device of claim 11 wherein
 the scanner aperture is approximately 13 cm in diameter.

13. A solar calibration method comprising the steps of:
 transmitting solar irradiance into a housing using a deployable door disposed at one portion of the housing and an aperture disposed at another portion of the housing;
 reflecting the transmitted solar irradiance, using a solar diffuser disposed within the housing, when the deployable door is in an open position;
 receiving, by a remote sensor, reflected solar irradiance from the solar diffuser, the reflected solar irradiance being a spectral standard for the remote sensor;
 receiving, by a solar diffuser monitor, reflected solar irradiance from the solar diffuser for calibration of the solar diffuser,
 receiving, by the solar diffuser monitor, solar irradiance directly from the aperture for calibrating solar diffuser monitor detectors based on the directly received solar irradiance; and
 pivoting the solar diffuser monitor between first and second positions,
 wherein the first position receives the diffusely reflected solar irradiance from the solar diffuser, and the second position receives the solar irradiance directly from the sun through the aperture.

14. The method of claim 13 wherein
 the steps of receiving the solar irradiance by the solar diffuser monitor includes detecting the solar irradiance at wavelengths, respectively tuned to a center wavelength of 0.47, 0.64, 0.86 and 1.38 microns.

15. The method of claim 13 wherein
 the steps of receiving the solar irradiance by the remote sensor includes detecting the solar irradiance at wavelengths, respectively tuned to a center wavelength of 0.47, 0.64, 0.86 and 1.38 microns.

16. The method of claim 13 further comprising
 the step of trending measurements of solar irradiance from the solar diffuser received by the solar diffuser monitor and comparing the measurements to solar irradiance measurements received by the remote sensor.

17. A method of calibrating a diffusive surface of a solar calibration device comprising the steps of:
 (a) positioning a remote sensor to receive reflected solar radiation from a diffusive surface for calibration of the remote sensor;
 (b) positioning a monitor to a first position to receive direct solar radiation for calibration of the monitor;
 (c) positioning the monitor to a second position to receive a dark spectral measurement of the diffusive surface;
 (d) deploying a door to an open position to expose the diffusive surface to solar irradiance;

(e) simultaneously measuring spectral values, using the remote sensor and the monitor, of radiation reflected from the diffusive surface;
(f) deploying the door to a closed position; and
(g) positioning the monitor to a third position being a stowed position.

18. The method of claim 17 wherein
step (b) is performed only during equinoxes.

19. The method of claim 17 wherein steps (c), (d) and (e) are performed in sequence, after performing step (a).

* * * * *